Figure 1:
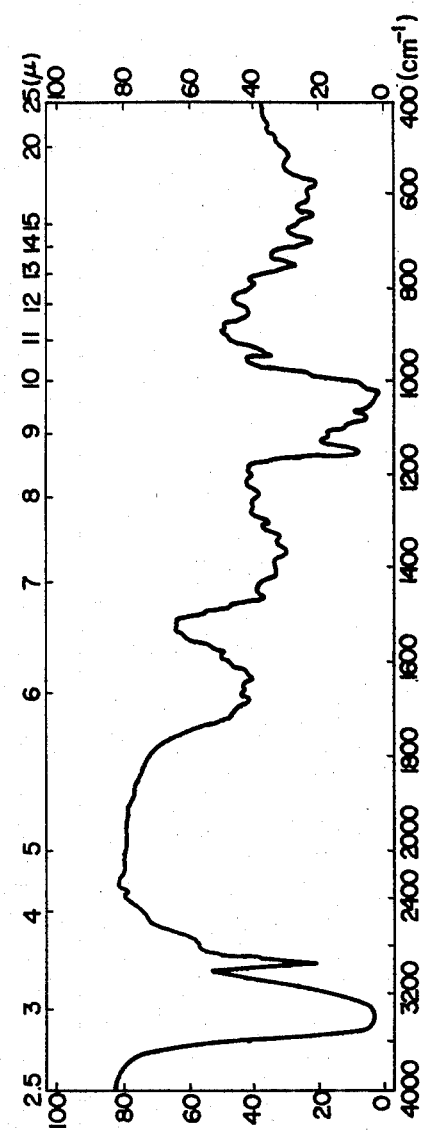

United States Patent [19]

Yamahira et al.

[11] 4,352,793

[45] Oct. 5, 1982

[54] PHARMACEUTICAL COMPOSITION COMPRISING BENCYCLANE FUMARATE AND CYCLODEXTRIN

[75] Inventors: Yoshiya Yamahira, Ibaraki; Takeshi Noguchi, Takatsuki; Keiji Fujioka, Ibaraki; Tetsuo Noguchi, Suita; Shigeji Sato, Ibaraki, all of Japan

[73] Assignee: Sumitomo Chemical Company, Limited, Osaka, Japan

[21] Appl. No.: 138,562

[22] Filed: Apr. 8, 1980

[30] Foreign Application Priority Data

Apr. 26, 1979 [JP] Japan .................................. 54-52164
Dec. 4, 1979 [JP] Japan ................................. 54-157151
Jan. 28, 1980 [JP] Japan .................................... 55-9201
Feb. 13, 1980 [JP] Japan ................................... 55-17042

[51] Int. Cl.$^3$ .......................................... A61K 31/715
[52] U.S. Cl. .................................. 424/180; 424/330; 424/316; 424/325
[58] Field of Search ............... 424/180, 316, 325, 330, 424/361; 536/112, 103

[56] References Cited
U.S. PATENT DOCUMENTS 4,228,160 10/1980 Szejtli et al. ......................... 424/180

FOREIGN PATENT DOCUMENTS 51-26215  3/1976  Japan .
53-10128  11/1978 Japan .
54-62313  4/1979  Japan .
54-86607  10/1979 Japan .
54-117018 11/1979 Japan .

OTHER PUBLICATIONS

Hennrich and Cramer, J. Am. Chem. Soc., vol. 85, 1/21–1/26, 1965.
Naoki, N., et al., Chem. Pharm. Bull., vol. 26, pp. 3609–3612 (1978).
Szejtli, J., et al., Acta Chimica Academiae Scientiarum Hungarical, vol. 99, pp. 433–446 (1979).
Kurozumi, M., et al., Chem. Pharm. Bull., vol. 23, pp. 3062–3068 (1975).

*Primary Examiner*—Blondel Hazel
*Attorney, Agent, or Firm*—Stevens, Davis, Miller & Mosher

[57]  ABSTRACT

A composition comprising as the pharmaceutically active ingredient bencyclane fumarate and cyclodextrin.

As compared with prior bencyclane fumarate preparations, this composition can greatly decrease the adverse effects of bencyclane fumarate and, in addition, offers considerable advantages from the viewpoints of method of use and method of production of preparation.

21 Claims, 9 Drawing Figures

PHARMACEUTICAL COMPOSITION COMPRISING BENCYCLANE FUMARATE AND CYCLODEXTRIN

This invention relates to a pharmaceutical composition comprising bencyclane fumarate and cyclodextrin as the main ingredients and to a process for producing the same.

Bencyclane, i.e. 3-[(1-benzylcycloheptyl)oxy]-N,N-dimethylpropylamine, is an excellent drug having anticonvulsant and vasodilative activities developed by Pallos et al. (Hungarian Pat. No. 151,865 (1965)). At present, it has been commercialized in the form of fumaric acid salt and used for medical purposes. As yet it is not satisfactory because this compound has various drawbacks as mentioned below, so that formulation of this compound into a pharmaceutical preparation has been restricted in many respects. Bencyclane fumarate has been used in the medical field for oral administration or for injection, its use however has been accompanied by various problems. Bencyclane fumarate is unstable and markedly decomposable under an acidic condition of pH 1-2. And it is also known that it decreases the gastric emptying rate when administered orally and, as a result, only a low blood concentration is obtained and no sufficient clinical effect can be expected if it is administered as a usual non-enteric coated preparation.

Further, bencyclane fumarate has a strong irritant action so that it causes considerable problems or a sense of irritation in the digestive tract. On the other hand, suppositories of bencyclane fumarate have already been prepared for the purpose of overcoming the various adverse effects and problems arising by the use of oral preparation (Japanese Patent Kokai (Laid-Open) No. 26,215/1976). Even in such preparations, however, the irritant character is maintained. Further, bencyclane fumarate itself has insufficient solubility for use as an injection. Therefore, it has to be solubilized by the addition of a surfactant or the like of which safety for use in injections has been recently disputed. Still further, bencyclane fumarate has a marked hemolytic character. For this reason, the bencyclane fumarate preparation for injection has not been commercialized in, for example, Japan.

An extensive study has been made in order to overcome the above drawbacks of bencyclane fumarate. As a result, it has now been found that these drawbacks of the bencyclane fumarate can be overcome by using the bencyclane fumarate in combination with cyclodextrin.

Thus, one object of this invention is to provide a bencyclane fumarate composition useful for medical use, and another object is to provide a process for producing said composition. Further objects will be apparent from the following description. In order to accomplish these objects, the present invention provides a pharmaceutical composition comprising, as the pharmaceutically active ingredients, bencyclane fumarate and cyclodextrin and, if necessary, a pharmaceutically acceptable inert carrier, and a process for producing said composition which comprises mixing together bencyclane fumarate and cyclodextrin.

The bencyclane fumarate composition of this invention has the following characteristic properties owing to which all the problems mentioned above can be solved at once.

The bencyclane fumarate composition of this invention is remarkably less irritant (cf. Experimental Example 1-a, b) and delays gastric emptying rate for less (cf. Experimental Example 3) than bencyclane fumarate itself. Further, the bencyclane fumarate composition of this invention is quite stable even in the strongly acidic region of pH 1 (cf. Experimental Example 4-a, b, c), and it displays amply sufficient absorbability from the intestinal tract in spite of the fact that, in the composition of the present invention, bencyclane fumarate is partially or wholly included in cyclodextrin at the time of administration as mentioned later (cf. Experimental Example 5).

Accordingly, the bencyclane fumarate composition of the present invention is advantageous in that the adverse effects are greatly decreased and in that it is easily administered and in that the cost for producing it is lowered.

The bencyclane fumarate composition of the present invention comprises an effective amount of bencyclane fumarate and cyclodextrin, to which various pharmacologically acceptable additives and excipients may be added if necessary. It is used in the form of a preparation for oral administration such as a capsule, powder, tablet, syrup or the like obtainable from the abovementioned mixture by the conventional procedure.

The bencyclane fumarate composition of the present invention can also be used for oral administration as a sustained release product. For example, it may be formed into tablets together with a binder such as sodium alginate, CMC-Na or the like, or it may be formed into granules and then coated with a film of wax, a cellulose derivative, a fatty acid ester, a synthetic polymer or the like, or it may be formulated for this purpose by other conventional methods.

Further, the bencyclane fumarate composition of the present invention can apply other dosage forms used for other administration routes.

Suppositories of the bencyclane fumarate composition of this invention are free from irritation and can be evaluated as having a quite high practical value (cf. Experimental Example 6-a, b). Said suppositories can be prepared by adding an effective amount of bencyclane fumarate and cyclodextrin and, if necessary, various pharmacologically acceptable additives to a conventional water-soluble or fatty base and then processing the mixture by the usual method.

Further, the bencyclane fumarate composition of this invention is soluble enough for injection preparations over a wide pH range (cf. Experimental Example 7-a, b). Further, the bencyclane fumarate composition of this invention shows markedly improved hemolytic activity (Experimental Example 8), so that an injection prepared from the bencyclane fumarate composition of this invention requires no surfactant and is highly safe and has a high practical value. This injection can be prepared by adding, if necessary, pharmacologically acceptable additives, an isotonizing agent, a pH regulator or the like to a pharmaceutically effective amount of bencyclane fumarate and cyclodextrin and processing the mixture by the conventional process of preparing injections.

Next, when the bencyclane fumarate composition of this invention is applied for an external use such as an ointment, solution or the like, its excellent properties such as its non-irritant character, stability, solubility and the like are very advantageous for the control of quality and for the production of such preparations. The external drugs such as ointments solutions and the like can be prepared by adding an effective amount of bencyclane fumarate and cyclodextrin and, if necessary, pharmacologically acceptable additives to the conventional base or solvent and then processing the mixture in the usual way.

The process for preparing the bencyclane fumarate composition of this invention is described below.

The cyclodextrin usable in this invention is cyclic dextrin obtainable by treating starch or dextrin with a certain kind of amylase and it is characterized by a doughnut-like molecular structure and a cavity having a diameter of 6–10 A inside itself. The cyclodextrin is classified into three types, i.e. α-, β- and γ-types according to the number of D-glucose units.

In this invention, any of these types may be used and their mixtures may also be used. Considering the effect and cost, however, β- and γ-cyclodextrins are preferable and β-cyclodextrin is particularly preferable.

In preparing the composition of this invention, said cyclodextrin and bencyclane fumarate are mixed together. This can be accomplished by various processes, and any process may be employed so long as bencyclane fumarate and cyclodextrin can be contacted sufficiently under the conditions of the process employed. However, the following process is preferable from the viewpoint of mixing them with greater certainty and simplicity. Thus, (1) cyclodextrin and bencyclane fumarate are mixed and the resulting mixture is kneaded together with water or a mixture of water and one or more kinds of organic solvents miscible with water. Otherwise, cyclodextrin is mixed with the above-mentioned solvent to give a paste, and the intended proportion of bencyclane fumarate dissolved in a small quantity of organic solvent miscible with water or not dissolved in solvent is added to the paste, after which the resulting mixture is thoroughly kneaded. The period of time of kneading is about 0.1–12 hours. The temperature of kneading may be selected arbitrarily, and room temperature may be enough for this purpose. The paste thus obtained is then dried by, for example, spray drying. At this stage, additives may be added to the kneaded paste, if necessary. (2) Alternatively, bencyclane fumarate and cyclodextrin are dissolved in water or a solvent mixture comprising water and one or more kinds of organic solvents miscible with water preferably at an elevated temperature. Otherwise, bencyclane fumarate dissolved or not dissolved in an organic solvent miscible with water is added to a solution of cyclodextrin in water or a solvent mixture comprising water and one or more kinds of organic solvents miscible with water and the resulting mixture is made into a homogeneous solution preferably at an elevated temperature. In this case, the concentration of bencyclane fumarate most preferably ranges between 0.3 and 10%. Though the temperature of heating may be selected arbitrarily and room temperature may be also enough for the purpose, an elevated temperature of about 60° C. is more preferable. The solution thus obtained is filtered, if necessary, and if the solution contains an organic solvent, the organic solvent is distilled off under a reduced pressure. Subsequently, the residue is dried by an appropriate drying process such as air flow drying, spray drying, freeze-drying, vacuum drying or the like. It is also possible to add additives, excipient, base and the like in the course of making preparations in accordance with the intended form of composition. Examples of the said organic solvents miscible with water used in the above-mentioned processes (1) and (2) include methyl alcohol, ethyl alcohol, n-propyl alcohol, isopropyl alcohol, acetone, dimethylformamide, dimethyl sulfoxide and the like and their mixtures. (3) Alternatively, bencyclane fumarate and cyclodextrin may be mixed and pulverized in a pulverizing machine. At this stage, additives may be added, if necessary. The pulverizing machine used for mixing and pulverizing should crush and grind the material mechanically into fine particles. Examples of said machine include a rotary ball mill, vibrating ball mill, hammer mill and the like, of which selection may be arbitrary. Though the period of time of mixing and pulverizing may vary depending on the kind of pulverizing machine, the amount of sample, the power of pulverization and the like, it is usually in the range of about several minutes to several hours. If mixing and pulverizing is carried out for an excessively long period of time, it becomes disadvantageous from the viewpoint of energy efficiency and may affect the quality of the active ingredient.

Apart from the above, any other processes may be employed so long as bencyclane fumarate can come into sufficient contact with cyclodextrin. In any case, it seems to be preferable from the viewpoint of practicability or quality of resulting composition that the molar ratio of cyclodextrin to bencyclane fumarate be in the range of about 1:5 to 5:1. As mentioned later in the experimental examples, it is preferable that the molar ratio of cyclodextrin to bencyclane fumarate be in the range of about 1:2 to 2:1. Further, the bencyclane fumarate composition of this invention has the best quality when the molar ratio is about 1:1.

In the bencyclane fumarate composition of this invention thus obtained, bencyclane fumarate and cyclodextrin exist partially or wholly in the form of an inclusion compound. In Experimental Example 2, this fact can be verified by dissolving β-cyclodextrin and bencyclane fumarate into water so as to give a molar ratio of 1:1, stirring the solution and freeze-drying it to obtain an inclusion compound of bencyclane fumarate which is included at a molar ratio of 1:1. This inclusion compound is obtained by the same procedure as in sample D of Example 1, so that it has a substantially identical meaning with sample D.

Similarly, it was also found that, in the bencyclane fumarate compositions of this invention prepared by other procedures, bencyclane fumarate and cyclodextrin exist either partially or wholly in the form of their inclusion compound, as the disclosed general properties of cyclodextrin suggest.

Next, this invention will be explained more clearly with reference to the following experimental examples. The samples used in the experimental examples were all prepared in, or according to, Example 1 mentioned later.

The content of the drawings attached is as follows.

FIG. 1 is an infrared absorption spectrum (KBr method) of the compound prepared in Experimental Example 2.

Figure 2:
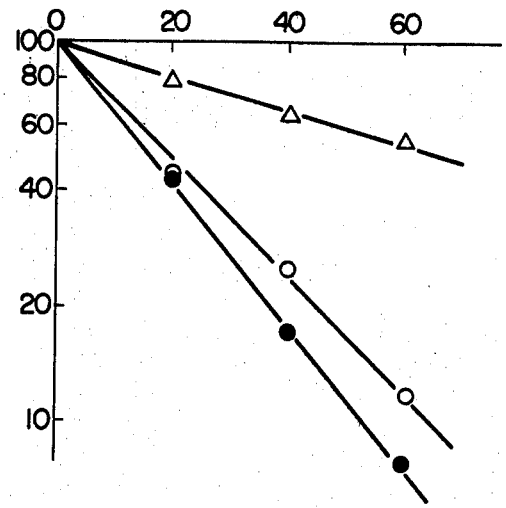

FIG. 2 illustrates the effects of bencyclane fumarate and the bencyclane fumarate composition of this invention (sample D) on the gastric emptying rate in terms of portion of gastric retention of sulfaguanidine as a function of time, wherein:
ordinate: portion of gastric retention (%)
abscissa: time (minutes) after oral administration,
△: sulfaguanidine + bencyclane fumarate,
○: sulfaguanidine + the bencyclane furmarate composition of this invention (sample D), and
●: sulfaguanidine alone.

Figure 3:
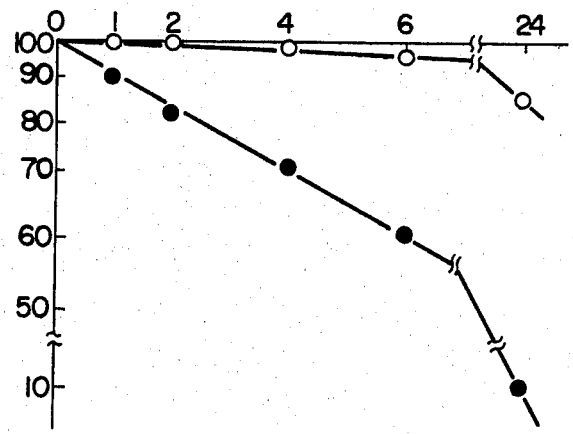

In FIG. 3, the stability of bencyclane fumarate is compared with that of the bencyclane fumarate composition of this invention (sample D) in 0.1 N hydrochloric acid by the methyl orange complex method, wherein:
ordinate: result of quantitative analysis (%),
abscissa: time (hours),
○: the bencyclane fumarate composition of this invention (sample D), and
●: bencyclane fumarate.

In FIGS. 4, 5, 6, 7 and 8, the stability of bencyclane fumarate is compared with the stabilities of the bencyclane fumarate compositions of this invention (samples D, H, I, J and N) in 0.1 N hydrochloric acid by gas chromatography, wherein:

ordinate: result of quantitative analysis (%),
abscissa: time (hours),
○: the bencyclane fumarate composition of this invention (FIGS. 4, 5, 6, 7 and 8 illustrates the case of samples D, H, I, J and N, respectively), and
●: bencyclane fumarate.

Figure 9:
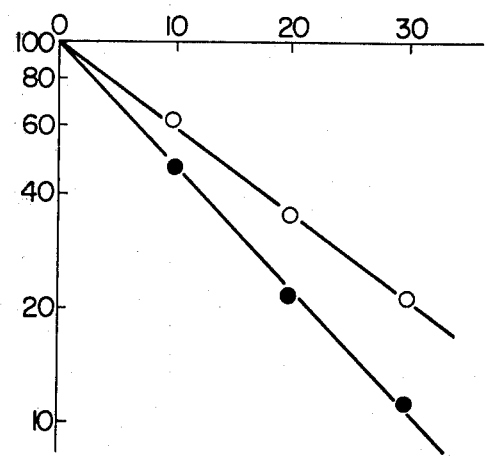

In FIG. 9, the absorbability from the digestive tract of bencyclane fumarate is compared with that of the bencyclane fumarate composition of this invention (sample D) in terms of portion of retention in the rat small intestine wherein:
ordinate: portion of retension in small intestine (%),
abscissa: time (minutes),
○: the bencyclane fumarate composition of this invention (sample D), and
●: bencyclane fumarate.

EXPERIMENTAL EXAMPLE 1-a

In order to compare the irritativity of the bencyclane fumarate composition of this invention with that of bencyclane fumarate, an administration test into rabbits' eye was carried out by the following method. Thus, bencyclane fumarate and the bencyclane fumarate compositions of this invention (samples A–J of Example 1) were separately added to pH 7.0 isotonic buffer solution to give solutions having a bencyclane fumarate concentration of 2–20,000 μg/ml, with which a crossover test was carried out by using three rabbits at every dosage level. After dropping one drop (about 25 μ-liter), the state of the eye was observed and the result was evaluated according to the following three-rank criterion: no change (0), winking (1), and keeping closed for 5 seconds or longer (2). The irritativity was determined based on the total score.

The results are as shown in Table 1. All the bencyclane fumarate compositions of which bencyclane fumarate:β-cyclodextrin molar ratio falls in the range of 1:5 to 5:1 show a significant decrease of irritativity as compared with bencyclane fumarate. Particularly, compositions having bencyclane fumarate:β-cyclodextrin molar ratios of 1:1 and 1:2 show no irritativity at all even at a high concentration of 20,000 μg/ml, suggesting that their structure is different from that of bencyclane fumarate in aqueous solution. The bencyclane fumarate-cyclodextrin composition having the ratio of 2:1 followed the abovementioned compositions in the lowness of irritativity.

(Note 1): The values of bencyclane fumarate shown in Table 1 are the averages of total scores for the irritativity of bencyclane fumarate found in the crossover tests using samples A–J.

(Note 2): In this experiment the right and left eyes of three animals are used so that the score takes the maximum value of 12 when both eyes of the three animals feel an intense irritation.

TABLE 1

| Concentration of active ingredient (expressed as bencyclane fumarate) | Irritativities of bencyclane fumarate compositions to the eye of the rabbit |||||||||||
|---|---|---|---|---|---|---|---|---|---|---|---|
| | Sample ( ): Molar ratio of bencyclane fumarate:β-cyclodextrin |||||||||||
| | Bencyclane fumarate | A (1:5) | B (1:3) | C (1:2) | D (1:1) | E (2:1) | F (3:1) | G (5:1) | H (1:1) | I (1:1) | J (1:1) |
| 2 μg/ml | 0 | 0 | 0 | 0 | 0 | 0 | 0 | 0 | 0 | 0 | 0 |
| 20 μg/ml | 0 | 0 | 0 | 0 | 0 | 0 | 0 | 0 | 0 | 0 | 0 |
| 200 μg/ml | 3 | 0 | 0 | 0 | 0 | 0 | 0 | 0 | 0 | 0 | 0 |
| 2000 μg/ml | 9 | 0 | 0 | 0 | 0 | 0 | 0 | 0 | 0 | 0 | 0 |
| 5000 μg/ml | 11 | 4 | 3 | 0 | 0 | 2 | 6 | 8 | 0 | 0 | 0 |
| 20000 μg/ml | 12 | 8 | 9 | 0 | 0 | 5 | 9 | 10 | 0 | 0 | 0 |

EXPERIMENTAL EXAMPLE 1-b

Samples M, N and O in Example 1 were evaluated with three rabbits in the same manner as in Experimental Example 1-a.

The results are as shown in Table 2. All the bencyclane fumarate compositions having a bencyclane fumarate:γ-cyclodextrin molar ratio of 1:2 to 2:1 show a significant decrease of irritativity as compared with bencyclane fumarate.

(Note 1): The values of bencyclane fumarate shown in Table 2 are the averages of total score for the irritativity of bencyclane fumarate found in the crossover tests using samples M, N and O.

TABLE 2

| Concentration of active ingredient (expressed as bencyclane fumarate) | Irritativities of bencyclane fumarate compositions to rabbits ||||
|---|---|---|---|---|
| | Sample ||||
| | Bencyclane fumarate | M (1:2) | N (1:1) | O (2:1) |
| 2 μg/ml | 0 | 0 | 0 | 0 |
| 20 μg/ml | 1 | 0 | 0 | 0 |
| 200 μg/ml | 3 | 0 | 0 | 0 |
| 2,000 μg/ml | 9 | 0 | 0 | 2 |
| 5,000 μg/ml | 12 | 0 | 0 | 6 |
| 20,000 μg/ml | 12 | 0 | 0 | 10 |

Note: ( ) represents molar ratio of bencyclane fumarate to γ-cyclodextrin.

EXPERIMENTAL EXAMPLE 2

A bencyclane fumarate-cyclodextrin inclusion compound having a molar ratio of 1:1 was prepared by dissolving 1.22 g of bencyclane fumarate and 3.40 g of β-cyclodextrin (corresponding to a molar ratio of 1:1) into 200 ml of water, stirring the solution at room temperature for about 60 minutes and then freeze-drying it.

The content of bencyclane fumarate in this sample was measured by gas chromatography, and it was found to be 25.4%. In the measurement with a differential scanning calorimeter, no endothermic peak was observed at all in the neighborhood of 131° C. (the melting point of bencyclane fumarate). In the melting point measurement, no remarkable change was observed in the neighborhood of 270°-280° C. (the melting point of β-cyclodextrin).

Measurement of specific rotary power revealed that $[\alpha]_D^{25} = +151.5°$ (1 g after dryness, water 100 ml, 100 mm). A measurement of elliptic rate in the circular dichroism revealed that $\theta = 0.004°$ (the measurement was carried out at 218 nm after dissolving the test compound at 25° C. into a solvent obtainable by adding 0.2 M KCl to 0.01 M phosphate buffer of pH 7.4 so as to give a concentration (calculated as bencyclane fumarate) of $10^{-4}$ M).

The infrared absorption spectrum of this compound is shown in FIG. 1.

The above sample was prepared by the same procedure as sample D of Example 1.

EXPERIMENTAL EXAMPLE 3

In order to compare the delaying action of gastric emptying of the bencyclane fumarate composition of this invention with that of bencyclane fumarate, the following experiments were carried out.

Sulfaguanidine was orally administered to three rats in combination with bencyclane fumarate or the bencyclane fumarate composition of this invention (sample D having a bencyclane fumarate:β-cyclodextrin molar ratio of 1:1). After a definite time, the animals were killed and the amount of sulfaguanidine remaining in the stomach was measured. As a control, sulfaguanidine alone was given to three rats and its amount remaining in the stomach was also measured. The concentration of active ingredients were 1 mg/ml as for bencyclane fumarate and 2.1 mg/ml as for sulfaguanidine. 0.4 ml of the solution was orally administered per head of rat.

The results are shown in FIG. 2. As is apparent from FIG. 2, bencyclane fumarate decreases the gastric emptying rate of sulfaguanidine, while the bencyclane fumarate composition of this invention (sample D) hardly decreases the gastric emptying rate. Similar results are obtained when bencyclane fumarate:β-cyclodextrin molar ratio is 1:2 (sample C) and 2:1 (sample E). No significant difference is observable between 1:1, 1:2 and 2:1.

EXPERIMENTAL EXAMPLE 4-a

In order to compare the stabilities in the stomach and intestine, the following experiments were carried out.

Figure 4:
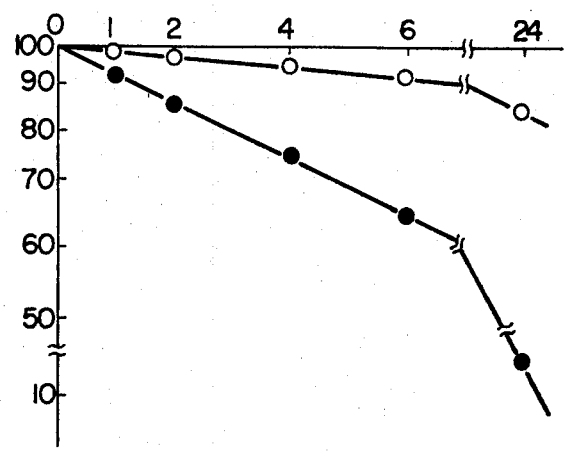

Bencyclane fumarate and sample D (molar ratio of bencyclane fumarate to β-cyclodextrin; 1:1) were separately dissolved into solution II of the disintegration test defined in The Japanese Pharmacopoeia Ed. IX having a pH value of 7.5 and 0.1 N hydrochloric acid so that the concentration, calculated as bencyclane fumarate, came to 200 mg/100 ml. The solutions were kept at 37° C., from which 1 ml of samples were taken at time intervals to carry out quantitative analysis by methyl orange complex method (Note 1) and gas chromatography (Note 2). As shown in FIGS. 3 and 4, the composition of this invention was remarkably superior to bencyclane fumarate in stability, under acidic conditions. At pH 7.5, the composition of this invention maintained just the same stability as bencyclane fumarate and kept entirely stable at 37° C. for 24 hours.

(Note 1): Potassium hydrogen phthalate buffer solution (ph 5.6) and a methyl orange solution were added to each sample and then extracted with chloroform. The extract was mixed with methanolic hydrochloric acid, and its absorbance was measured at a wavelength of 525 mμ.

(Note 2): Each sample was alkalified with NaOH, extracted with chloroform and evaporated to dryness. After adding carbetapentane citrate as an internal standard, the residue was quantitatively analyzed by gas chromatography.

EXPERIMENTAL EXAMPLE 4-b

Figure 5:
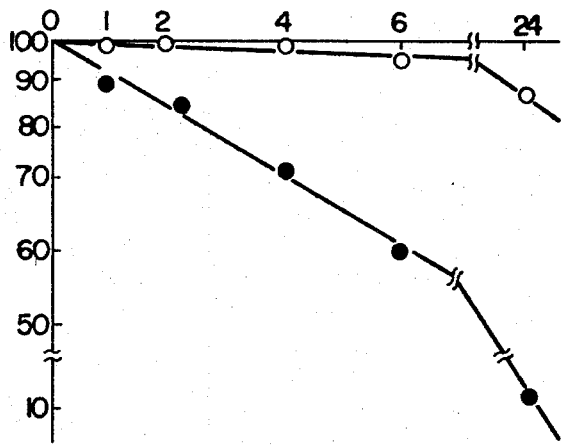
Figure 6:
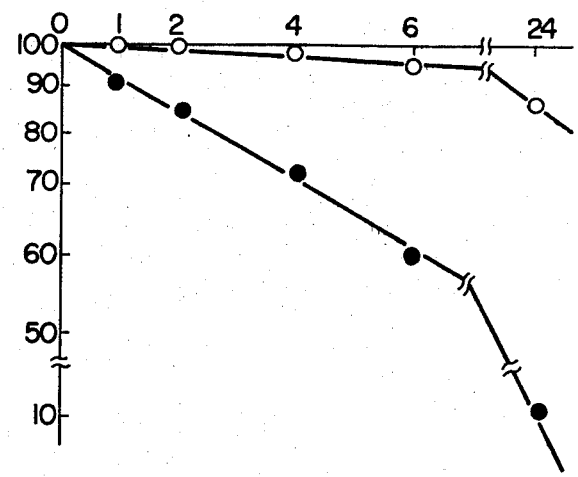
Figure 7:
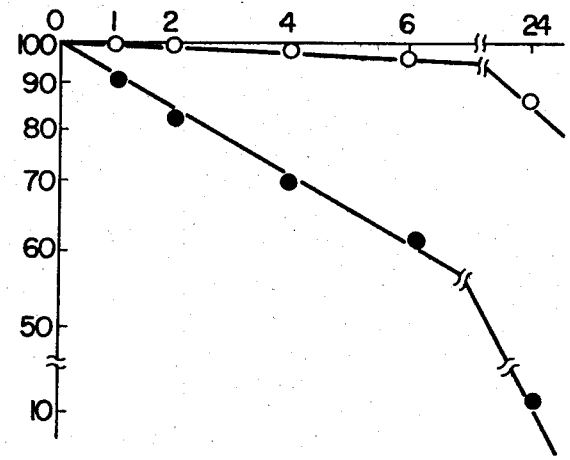

In the same manner as in Experimental Example 4-a, the stabilities of samples H, I and J of Example 1 in acidic solution were measured by gas chromatography. For any sample, the results obtained were comparable to those in Experimental Example 4-a as shown in FIGS. 5-7.

EXPERIMENTAL EXAMPLE 4-c

Figure 8:
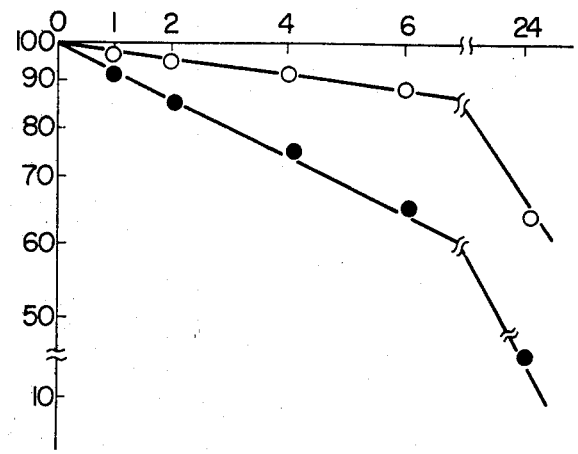

In the same manner as in Experimental Example 4-a, the stability of sample N of Example 1 in acidic solution was measured by gas chromatography. As shown in FIG. 8, it was remarkably more stable than bencyclane fumarate. However, stability was somewhat inferior that of β-cyclodextrin mentioned in Experimental Examples 4-a and 4-b.

EXPERIMENTAL EXAMPLE 5

In order to compare the absorbability from the digestive tract of the bencyclane fumarate composition of this invention with that of bencyclane fumarate, an absorption experiment was carried out with three rats per one group by the use of a small intestinal loop. Rats anesthesized with sodium pentobarbital were subjected to abdominal incision in order to form a small intestinal loop. 5 Ml of sample solution was administered into the loop. After a definite time, the inside of loop was washed to recover the remaining drug and analyze it quantitatively. The quantitative analysis was carried out by gas chromatography. The concentration of administered drug was 1 mg/ml as bencyclane fumarate. The results are shown in FIG. 9.

As shown in FIG. 9, bencyclane fumarate is quite excellent in absorbability and 50% of the amount administered can be absorbed in 10 minutes. By contrast, the bencyclane fumarate composition of this invention (sample D having bencyclane fumarate:β-cyclodextrin molar ratio of 1:1) shows a tendency of somewhat slower absorption. Nevertheless, its absorption rate is still high and presents no problem. In the same manner, the rates of absorption of other compositions having different molar ratios were also measured to reveal that no significant difference can be observed between molar ratios of 1:2, 2:1 and 1:1.

EXPERIMENTAL EXAMPLE 6-a

In order to compare the irritant properties of suppositories, suppositories containing 50 mg of bencyclane fumarate, sample C or sample D (calculated as bencyclane fumarate) were prepared by using Witepsol W-35 base (triglyceride of higher fatty acid manufactured by Dynamite Novel Co.). The suppositories were applied to four healthy adult male persons to investigate the feeling in use. It was found that, as shown in Table 3, the irritative feeling quite markedly decreases when the bencyclane fumarate composition of this invention is used.

TABLE 3

| Feeling in use | Sample C (molar ratio 1:2) | Sample D (molar ratio 1:1) | Bencyclane fumarate |
|---|---|---|---|
| A little pain | 1 person | 0 person | 0 person |
| A burning pain | 0 | 0 | 4 |
| A warm feeling | 1 | 1 | 0 |
| An intense gripe | 0 | 0 | 4 |
| No particular feeling | 2 | 3 | 0 |

EXPERIMENTAL EXAMPLE 6-b

Sample O of Example 1 was evaluated in the same manner as in Experimental Example 6-a. As shown in Table 4, it was roughly equal to samples C and D.

TABLE 4

| Feeling in use | Sample O (molar ratio 2:1) | Bencyclane fumarate |
|---|---|---|
| A little pain | 1 person | 0 person |
| A burning pain | 0 | 4 |
| A warm feeling | 1 | 0 |
| An intense gripe | 0 | 4 |
| No particular feeling | 2 | 0 |

EXPERIMENTAL EXAMPLE 7-a

In order to compare the solubilities, the following experiment was carried out with the samples of Example 1.

Each sample was added to solution I of the disintegration test defined in the Japanese Pharmacopoeia Ed. IX (pH 1.2), solution II of the same (pH 7.5) and water in excess to saturation and the resulting mixtures were shaken at room temperature for 30 minutes. They were centrifuged at 2,500 rpm for 10 minutes, the supernates were taken out and appropriately diluted, and they were quantitatively analyzed by UV measurement. The results are shown in Table 5. The composition of this invention exhibits a higher solubility than that of bencyclane fumarate over a wide pH range, particularly, in the case of the composition having a molar ratio of 1:1.

TABLE 5

| Sample | Solution I | Water | Solution II |
|---|---|---|---|
| A (1:5) | 5.5 mg/ml[*1] | 6.1 | 6.8 |
| B (1:3) | 9.9 | 10.9 | 13.7 |
| C (1:2) | 28.6 | 28.3 | 22.9 |
| D (1:1) | 81.0 | 63.7 | 92.3 |
| E (2:1) | 31.1 | 21.9 | 29.2 |
| F (3:1) | 28.6 | 17.1 | 29.7 |
| G (5:1) | 27.8 | 14.5 | 29.0 |
| Bencyclane fumarate | 21.5 | 9.7 | 22.2 |

[*1]: All the values are calculated as bencyclane fumarate.

EXPERIMENTAL EXAMPLE 7-b

In order to compare the solubilities, the following experiment was carried out in the same manner as in Experimental Example 7-a by using the samples shown in Table 6.

The samples were separately added to water in excess to saturation and the resulting mixtures were shaken at room temperature for 30 minutes. They were centrifuged at 2,500 rpm for 10 minutes, and the supernates were taken out, appropriately diluted and quantitatively analyzed by UV measurement. The results were as shown in Table 6. The solubility is particularly higher in sample N than in bencyclane fumarate.

TABLE 6

| Sample | Water |
|---|---|
| M (1:2) | 21.4 mg/ml[*1] |
| N (1:1) | 105.4 |
| O (2:1) | 28.4 |
| Bencyclane fumarate | 9.7 |

[*1]: All the values are calculated as bencyclane fumarate.

EXPERIMENTAL EXAMPLE 8

In order to compare the influence exercised on hemolytic property, the samples shown in Table 7 were subjected to the experiment according to the method of Akaishi et al. (Note 1) with fresh blood of a rabbit.

As is apparent from the results shown in Table 7, a remarkable improvement can be observed in the composition of this invention.

TABLE 7

| | 1 mg/ml (Note 2) | 3 mg/ml (Note 3) |
|---|---|---|
| Sample C (1:2) | No hemolysis | Hemolysis No color change |
| Sample D (1:1) | " | Hemolysis No color change |
| Sample F (3:1) | Slight hemolysis | Hemolysis Slight color change |
| Bencyclane fumarate | Hemolysis | Intense hemolysis Color change |

(Note 1) Gekkan Yakuji, Vol. 16, No. 6, Page 901 (1974).
(Note 2) Each sample was made into a solution having a concentration of 1 mg/ml calculated as bencyclane fumarate.
(Note 3) Each sample was made into a solution having a concentration of 3 mg/ml calculated as bencyclane fumarate.

Next, the examples of this invention will be mentioned below. This invention is not limited by these examples. In preparing the compositions of Example 4 and below, the samples of Example 1 or similar samples prepared in a larger quantity according to the method of Example 1 were used.

EXAMPLE 1

The following compositions of this invention having various formulations were prepared by the methods mentioned below.

A. A composition having a bencyclane fumarate:β-cyclodextrin molar ratio of 1:5 was prepared by dissolving 0.12 g of bencyclane fumarate and 1.70 g of β-cyclodextrin into 100 ml of water and freeze-drying the resulting solution.

B. A composition having a bencyclane fumarate:β-cyclodextrin molar ratio of 1:3 was prepared by dissolving 0.20 g of bencyclane fumarate and 1.70 g of β-cyclodextrin into 100 ml of water and freeze-drying the resulting solution.

C. A composition having a bencyclane fumarate:β-cyclodextrin molar ratio of 1:2 was prepared by dissolving 0.30 g of bencyclane fumarate and 1.70 g of β-cyclodextrin into 100 ml of water and freeze-drying the resulting solution.

D. A composition having a bencyclane fumarate:β-cyclodextrin molar ratio of 1:1 was prepared by dissolving 0.61 g of bencyclane fumarate and 1.70 g of β-cyclodextrin into 100 ml of water and freeze-drying the resulting solution.

E. A composition having a bencyclane fumarate:β-cyclodextrin molar ratio of 2:1 was prepared by dissolving 0.61 g of bencyclane fumarate and 0.85 g of β-cyclodextrin into 100 ml of water and freeze-drying the resulting solution.

F. A composition having a bencyclane fumarate:β-cyclodextrin molar ratio of 3:1 was prepared by dissolving 0.61 g of bencyclane fumarate and 0.57 g of β-cyclodextrin into 100 ml of water and freeze-drying the resulting solution.

G. A composition having a bencyclane fumarate:β-cyclodextrin molar ratio of 5:1 was prepared by dissolving 0.61 g of bencyclane fumarate and 0.34 g of β-cyclodextrin into 100 ml of water and freeze-drying the resulting solution.

H. A composition having a bencyclane fumarate:β-cyclodextrin molar ratio of 1:1 was prepared by dissolving 200 g of bencyclane fumarate and 560 g of β-cyclodextrin into 10 liters of distilled water at 50° C. with heating, followed by filtering the resulting solution with a Millipore filter and spray-drying it.

I. A composition having a bencyclane fumarate: β-cyclodextrin molar ratio of 1:1 was prepared by placing 200 g of bencyclane fumarate and 560 g of β-cyclodextrin in a porcelain ball mill and mixing and pulverizing them for one hour.

J. A composition having a bencyclane fumarate: β-cyclodextrin molar ratio of 1:1 was prepared by mixing 2.0 kg of bencyclane fumarate with 5.6 kg of β-cyclodextrin, adding about 1.5 liters of water thereto, kneading the mixture for about 10 minutes and then drying it.

K. A composition having a bencyclane fumarate:β-cyclodextrin molar ratio of 1:1 was prepared by dissolving 0.61 g of bencyclane fumarate and 1.70 g of β-cyclodextrin into 100 ml of water and concentrating the resulting solution to dryness under a reduced pressure at a temperature of 35°-45° C.

L. A composition having a bencyclane fumarate:β-cyclodextrin molar ratio of 1:1 was prepared by dissolving 0.61 g of bencyclane fumarate and 1.70 g of β-cyclodextrin into 100 ml of 50 V/V % aqueous solution of ethanol with heating, followed by distilling off the solvent under a reduced pressure at about 60° C. and vacuum-drying the residue.

M. A composition having a bencyclane fumarate:γ-cyclodextrin molar ratio of 1:2 was prepared by dissolving 0.30 g of bencyclane fumarate and 1.95 g of γ-cyclodextrin into 100 ml of water and freeze-drying the resulting solution.

N. A composition having a bencyclane fumarate:γ-cyclodextrin molar ratio of 1:1 was prepared by dissolving 0.61 g of bencyclane fumarate and 1.95 g of γ-cyclodextrin into water and freeze-drying the resulting solution.

O. A composition having a bencyclane fumarate:γ-cyclodextrin molar ratio of 2:1 was prepared by dissolving 0.61 g of bencyclane fumarate and 0.98 g of γ-cyclodextrin into water and freeze-drying the resulting solution.

P. A composition having a bencyclane fumarate:γ-cyclodextrin molar ratio of 1:1 was prepared by dissolving 0.61 g of bencyclane fumarate and 1.95 g of γ-cyclodextrin into 100 ml of water and concentrating the resulting solution to dryness under a reduced pressure at a temperature of 35°-45° C.

Q. A composition having a bencyclane fumarate:γ-cyclodextrin molar ratio of 1:1 was prepared by mixing 0.61 g of bencyclane fumarate with 1.95 g of γ-cyclodextrin, adding about 3 ml of water thereto, kneading the mixture in a mortar for about 20 minutes and then drying it.

R. A composition having a bencyclane fumarate:γ-cyclodextrin molar ratio of 1:1 was prepared by mixing and pulverizing 0.61 g of bencyclane fumarate and 1.95 g of γ-cyclodextrin by means of a high speed vibrating sample pulverizer type of pulverizing machine for about 5 minutes.

S. A composition having a bencyclane fumarate:β-cyclodextrin molar ratio of 1:1 was prepared by mixing 0.61 g of bencyclane fumarate with 1.70 g of β-cyclodextrin, adding about 3 ml of water thereto, kneading the mixture in a mortar for about 20 minutes and then drying it.

EXAMPLE 2

1 kg of bencyclane fumarate and 3 kg of β-cyclodextrin were mixed together for 5 minutes. While adding an appropriate quantity of an aqueous alcoholic solution containing hydroxypropyl methyl cellulose, the mixture was kneaded for 10 minutes. The kneaded mixture was granulated in the wet state, dried for 20–30 minutes at 50° C. by means of a speed drier, passed through a 16 mesh sieve, mixed with 1.75% of magnesium stearate and then formed into tablets of 410 mg and 205 mg in weight.

EXAMPLE 3

1 kg of bencyclane fumarate and 3.2 kg of γ-cyclodextrin were mixed for 5 minutes. While adding an appropriate quantity of an aqueous alcoholic solution containing hydroxypropyl methyl cellulose, the mixture was kneaded for 10 minutes. The kneaded mixture was granulated in the wet state, dried for 20–30 minutes at 50° C. by means of a speed drier, passed through a 16 mesh sieve, mixed with 1.75% of magnesium stearate and then formed into tablets of 410 mg and 205 mg in weight.

EXAMPLE 4

| Sample I | 200 g |
|---|---|
| Magnesium stearate | 3 g |

The above-mentioned ingredients were mixed together, and the resulting powdery mixture was formed into a tablet of 195 mg in weight.

EXAMPLE 5

| Sample Q | 2,057 g |
|---|---|
| Crystalline cellulose | 2,343 g |
| Magnesium stearate | 50 g |
| Talc | 50 g |

The above-mentioned ingredients were mixed together, and the resulting powdery mixture was formed by the direct compression process into a tablet of 450 mg in weight.

EXAMPLE 6

| Sample S | 200 g |
|---|---|
| Lactose | 150 g |
| Corn starch | 95 g |
| Magnesium stearate | 5 g |

Among the above-mentioned ingredients, sample S, lactose and corn starch were mixed together, and the mixture was kneaded together with water and granulated. After drying the granule, it was mixed with magnesium stearate and formed into a tablet of 450 mg in weight.

EXAMPLE 7

| Sample H | 400 g |
|---|---|
| Lactose | 600 g |

A powdery composition was prepared by mixing the above-mentioned ingredients to give a uniform powdery mixture.

EXAMPLE 8

| Sample Q | 410 g |
|---|---|
| Mannit | 290 g |
| Lactose | 290 g |
| Hydroxypropyl cellulose | 10 g |

Among the above-mentioned ingredients, sample Q, mannit and lactose were mixed together. The mixture was kneaded together with a solution of hydroxypropyl cellulose in 30% aqueous alcohol. The kneaded mixture was granulated by means of an extrusion type granulator and then dried to give a granular composition.

EXAMPLE 9

| Sample I | 400 g |
|---|---|
| Mannit | 300 g |
| Lactose | 290 g |
| Hydroxypropyl cellulose | 10 g |

Among the above-mentioned ingredients, sample I, mannit and lactose were mixed together. The mixture was kneaded together with a solution of hydroxypropyl cellulose in 30% aqueous alcohol. The kneaded mixture was granulated by means of an extrusion type granulator and then dried to give a granular composition.

EXAMPLE 10

| Sample J | 800 g |
|---|---|
| Methyl cellulose | 50 g |
| Sugar | 2,000 g |
| Methylparaben | 5 g |
| Propylparaben | 2 g |
| Strawberry essence | 1 g |

The above-mentioned ingredients were successively added and the resulting mixture was diluted with water to a total volume of 10 liters to give a syrup composition.

EXAMPLE 11

The same ingredients as in Example 6 were taken in the same amounts, mixed with magnesium stearte by the same procedure and packed into No. 3 hard capsule to give a capsule composition.

EXAMPLE 12

| Sample I | 400 g |
|---|---|
| Corn oil | 600 g |
| Polyoxyethylene lauryl ether (Nikkol BL-4,2) | 20 g |

Polyoxyethylene lauryl ether was dissolved into corn oil. Sample I was added to the solution, mixed, and dispersed uniformly. 250 mg portions of the dispersion were packed into soft capsules for oral administration.

EXAMPLE 13

| Sample H | 200 g |
|---|---|
| Witepsol S-55 | 1,250 g |

Sample H was added to molten Witepsol S-55 and uniformly mixed. The mixture was filled into a suppository container to give a suppository.

EXAMPLE 14

| Sample P | 200 g |
|---|---|
| Witepsol W-35 | 1,250 g |

Sample P was added to molten Witepsol W-35 and uniformly mixed. The mixture was filled into a suppository container to give a suppository.

EXAMPLE 15

| Sample E | 5 g |
|---|---|
| Macrogol 4000 | 30 g |
| Macrogol 1000 | 15 g |
| Nikkol BO-20 | 2 g |

Nikkol BO-20 (polyoxyethylene oleyl ether) and Sample E were added to a molten mixture of Macrogol 4000 and Macrogol 1000 and uniformly mixed together. The resulting mixture was filled into a suppository container to give suppository.

EXAMPLE 16

6.1 g of bencyclane fumarate and 17 g of $\beta$-cyclodextrin were slowly dissolved into 305 ml of water with stirring and pH was adjusted to 6–7 with dilute aqueous solution of sodium hydroxide and dilute aqueous hydrochloric acid. This solution was aseptically filtered with a Millipore filter, and 5 ml portions of the filtrate were poured into vials and freeze-dried. Thus, a lyophilized injection of 100 mg/vial (as bencyclane fumarate) was obtained.

EXAMPLE 17

10.5% solution of sample R was adjusted to pH 6–7 with dilute aqueous solution of sodium hydroxide and dilute hydrochloric acid and then isotonized with sodium chloride. This solution was filtered with 0.45$\mu$ Millipore filter. The filtrate was filled into 2 ml ampoule and sterilized at 120° C. for 20 minutes. Thus, an injection of 50 mg (as bencyclane fumarate)/ampoule was obtained.

EXAMPLE 18

| Sample J | 3.8 g |
|---|---|
| Diisopropyl adipate | 25 g |
| Polyoxyethylene (15) cetyl ether | 2 g |
| Sorbitan monostearate | 1 g |
| Carboxyvinyl polymer | 0.4 g |
| Cetanol | 5 g |
| Diisopropanolamine | 1 g |
| Purified water | 61.8 g |

Among the above-mentioned ingredients, diisopropyl adipate, polyoxyethylene (15) cetyl ether, sorbitan monostearate, cetanol, carboxyvinyl polymer (aqueous solution) and sample J (aqueous solution) were mixed together and stirred at an elevated temperature to which was added an aqueous solution of diisopropanolamine. After cooling, there was obtained a creamy composition.

EXAMPLE 19

| Sample R | 4.2 g |
|---|---|
| Carboxyvinyl polymer | 1 g |
| Diisopropanolamine | 1 g |
| Propylene glycol | 5 g |
| Purified water | 89.2 g |

Among the above-mentioned ingredients, sample D was dissolved into purified water and mixed with propylene glycol. Then carboxyvinyl polymer was dispersed into the mixture and swollen with it, to which aqueous solution of diisopropanolamine was added. Thus, a gelatinous composition was obtained.

EXAMPLE 20

A mixture consisting of 3.8 g of sample H, 65 g of purified water and 5 g of propylene glycol was diluted with ethanol to a total volume of 100 ml. Thus, an external solution was obtained.

What is claimed is:

1. A pharmaceutical composition having anticonvulsant and vasodilatory activity comprising as a pharmaceutically active ingredient an effective amount of bencyclane fumarate and cyclodextrin in a molar ratio ranging between about 1:5 and 5:1.

2. A composition according to claim 1 wherein said composition comprises an inclusion compound of bencyclane fumarate and cyclodextrin.

3. A composition according to claim 1 or 2 wherein said cyclodextrin is β-cyclodextrin.

4. A composition according to claim 1 or 2 wherein said cyclodextrin is γ-cyclodextrin.

5. A composition according to claim 1 or 2 wherein the ratio of bencyclane fumarate to cyclodextrin is in the range of about 1:2 to 2:1 by mole.

6. A composition according to claim 1 or 2 wherein the ratio of bencyclane fumarate to cyclodextrin is about 1:1 by mole.

7. A process for producing the composition of claim 1, the process comprising mixing together bencyclane fumarate and cyclodextrin in said molar ratio.

8. A process according to claim 7, wherein the method of mixing comprises kneading bencyclane fumarate and cyclodextrin together with water or a solvent mixture comprising water and at least one organic solvent miscible with water.

9. A process according to claim 7, wherein the method of mixing comprises dissolving bencyclane fumarate and cyclodextrin into water or a solvent mixture comprising water and at least one organic solvents miscible with water.

10. A process according to claim 8 or 9, wherein said organic solvent miscible with water is selected from the group consisting of methanol, ethanol, acetone, n-propyl alcohol and isopropyl alcohol.

11. A process according to claim 7, wherein the method of mixing comprises mixing and pulverizing bencyclane fumarate and cyclodextrin.

12. A process according to any one of claims 7-9 and 11, wherein said bencyclane fumarate and said cyclodextrin are used in an amount expressed by a molar ratio of about 1:1.

13. A process according to any one of claims 7-9 and 11, wherein said cyclodextrin is β-cyclodextrin.

14. A process according to any one of claims 7-9 and 11, wherein said cyclodextrin is γ-cyclodextrin.

15. An inclusion compound of bencyclane fumarate and β-cyclodextrin.

16. An inclusion compound according to claim 15, wherein the ratio of bencyclane fumarate to β-cyclodextrin is about 1:1.

17. A composition according to claim 3 wherein the ratio of bencyclane fumarate to cyclodextrin is in the range of about 1:2 to 2:1 by mole.

18. A composition according to claim 4 wherein the ratio of bencyclane fumarate to cyclodextrin is in the range of about 1:2 to 2:1 by mole.

19. A composition according to claim 3 wherein the ratio of bencyclane fumarate to cyclodextrin is about 1:1 by mole.

20. A composition according to claim 4 wherein the ratio of bencyclane fumarate ty cyclodextrin is about 1:1 by mole.

21. A composition according to claim 5 wherein the ratio of bencyclane fumarate to cyclodextrin is about 1:1 by mole.

* * * * *